United States Patent [19]

Pocius

[11] Patent Number: 5,718,977
[45] Date of Patent: Feb. 17, 1998

[54] ORGANOBORANE POLYOXYALKYLENEPOLYAMINE COMPLEXES AND ADHESIVE COMPOSITIONS MADE THEREWITH

[75] Inventor: Alphonsus V. Pocius, Maplewood, Minn.

[73] Assignee: Minnesota Mining and Manufacturing Company, St. Paul, Minn.

[21] Appl. No.: 770,228

[22] Filed: Dec. 19, 1996

Related U.S. Application Data

[62] Division of Ser. No. 422,429, Apr. 14, 1995, Pat. No. 5,621,143.

[51] Int. Cl.$^6$ .................................................. B32B 27/30
[52] U.S. Cl. ................... 428/422; 428/421; 428/515; 428/516; 428/519; 428/520; 428/411.1; 156/332; 156/327; 526/198
[58] Field of Search ............................ 428/411.1, 421, 428/422, 515, 516, 519, 520; 156/332, 327

[56] References Cited

U.S. PATENT DOCUMENTS

| | | | |
|---|---|---|---|
| 2,985,633 | 5/1961 | Welch et al. | 260/85.3 |
| 3,141,862 | 7/1964 | Kirshenbaum et al. | 260/45.5 |
| 3,275,611 | 9/1966 | Mottus et al. | 260/80.5 |
| 3,340,193 | 9/1967 | Fields et al. | 252/56 |
| 3,418,260 | 12/1968 | Trofimenko | 260/2 |
| 3,425,988 | 2/1969 | German et al. | 260/47 |
| 3,451,952 | 6/1969 | Slocombe | 260/2.5 |
| 3,476,727 | 11/1969 | Lo Monaco et al. | 260/92.8 |
| 3,527,737 | 9/1970 | Masuhara et al. | 260/78.5 |
| 3,829,973 | 8/1974 | Masuhara et al. | 32/15 |
| 4,167,616 | 9/1979 | Bollinger | 526/197 |
| 4,515,724 | 5/1985 | Ritter | 260/410 |
| 4,638,092 | 1/1987 | Ritter | 568/1 |
| 4,639,498 | 1/1987 | Ritter | 526/196 |
| 4,676,858 | 6/1987 | Ritter | 156/307.3 |
| 4,775,734 | 10/1988 | Goel | 528/89 |
| 4,920,188 | 4/1990 | Sakashita et al. | 526/196 |
| 4,921,921 | 5/1990 | Ritter | 526/195 |
| 4,985,516 | 1/1991 | Sakashita et al. | 526/196 |
| 5,106,928 | 4/1992 | Skoultchi et al. | 526/196 |
| 5,143,884 | 9/1992 | Skoultchi et al. | 502/160 |
| 5,286,821 | 2/1994 | Skoultchi | 526/196 |
| 5,310,835 | 5/1994 | Skoultchi et al. | 526/198 |
| 5,376,746 | 12/1994 | Skoultchi | 526/196 |
| 5,401,805 | 3/1995 | Chung et al. | 525/288 |
| 5,539,070 | 7/1996 | Zharov et al. | 526/198 |

FOREIGN PATENT DOCUMENTS

| | | | |
|---|---|---|---|
| 2061021 | 10/1992 | Canada | C09D 157/00 |
| 46-16888 | 5/1971 | Japan | B01J 000/00 |
| 48-18928 | 6/1973 | Japan | C09J 5/00 |
| 53-102395 | 9/1978 | Japan | C08F 4/40 |
| 62-288675 | 12/1987 | Japan | C09J 3/14 |
| 3-177470 | 8/1991 | Japan | |
| 3-264509 | 11/1991 | Japan | A61K 6/00 |
| 93-235089 | 9/1993 | Japan | A61K 6/00 |
| 904403 | 8/1962 | United Kingdom | |
| 988632 | 4/1965 | United Kingdom | |
| 1113722 | 5/1968 | United Kingdom | C08F 1/28 |
| 1132261 | 10/1968 | United Kingdom | C08F 1/84 |

OTHER PUBLICATIONS

The Trialkylborane–initiated Graft Copolymerization of Methyl Methacrylate onto Hemoglobin, K. Kojima, S. Iwabuchi and K. Kojima, *Bulletin of the Chemical Society of Japan*, vol. 44, pp. 1891–1895 (1971).

A New Method for the Graft Copolyermerization of Methyl Methacrylate onto Proteins and Fibers, *Polymer Letters*, vol. 9, pp. 25–29 (1971).

The Grafting of Methyl Methacrylate onto Cotton by Tri–n–butylborane, K. Kojima, S. Iwabuchi, K. Murakami, K. Kojima and F. Ichikawa, *Journal of Applied Polymer Science*, vol. 16, pp. 1139–1148 (1972).

Grafting of Vinyl Monomers by Tri–n–Butylborane onto Chlorophyll and Related Compounds, *Polymer Letters Edition*, vol. 13, pp. 361–363 (1975).

Tributylborane–Initiated Grafting of Methyl Methacrylate onto Chitin, K. Kojima, M. Yoshikuni and T. Suzuki, *Journal of Applied Polymer Science*, vol. 24, pp. 1587–1593 (1979).

Grafting of Methyl Methacrylate onto Silk Fibers Initiated by Tri–n–Butylborane, M. Tsukada, T. Yamamoto, N. Nakabayashi, H. Ishikawa and G. Freddi, *Journal of Applied Polymer Science*, vol. 43, pp. 2115–2121 (1991).

Molecular Weight Distribution of the Methyl Methacrylate (MMA) Polymer Separated from the MMA–Grafted Silk Fiber, M. Tsukada, Y. Goto, G. Freddi, T. Yamamoto and N. Nakabayashi, *Jounal of Applied Polymer Science*, vol. 44, pp. 2197–2202 (1992).

Synthesis of Functionalized Polypropylene and Polypropylene–Polymethylmethacrylate Graft Copolymer, D. Rhubright and T.C. Chung, Proceedings of the American Chemical Society, *Polymeric Materials Science and Engineering*, vol. 67, pp. 112–113 (1992).

Polymerization of Acrylonitrile in Presence of Tributylborine, G. Kolesnikov and L. Fedorova, translated from *Bull. Acad. Sci. USSR, Div. Chem. Sci.*, p. 236 (1957).

Tributylborine: A Catalyst for the Polymermization of Unsaturated Compounds G. Kolesnikov and N.V. Klimentova, translated from *Bull. Acad. Sci. USSR, Div. Chem. Sci.*, p. 653 (1957).

Triethylboron as an Initiator for Vinyl Polymerization, J. Furukawa, T. Tsuruta and S. Inoue, *Journal of Polymer Science*, vol. XXVI, Issue No. 113, pp. 234–236 (1957).

(List continued on next page.)

*Primary Examiner*—Mark Nagumo
*Attorney, Agent, or Firm*—Gary L. Griswold; Walter N. Kirn; Steven E. Skolnick

[57] ABSTRACT

A complex comprises organoborane and polyoxyalkylenepolyamine. The complexes are useful in systems for initiating the polymerization of acrylic monomer, which systems further include an amine reactive compound. Polymerizable acrylic monomer compositions useful as adhesives can be prepared.

23 Claims, No Drawings

OTHER PUBLICATIONS

Oxygen Compounds as Cocatalyst for Triethylboron–Catalyzed Vinyl Polymerization, J. Furukawa and T. Tsuruta, *Journal of Polymer Science*, vol. XXVIII, Issue No. 116, pp. 227–229 (1958).

Mechanism of the Polymerization of Acrylonitrile in Presence of Tributylborine, G. Kolesnikov and L. Fedorova, translated from *Bull. Acad. Sci. USSR, Div. Chem. Sci.*, p. 906 (1958).

Mechanism of Trialkylboron Initiated Polymerization, J. Fordham and C. Sturm, *Journal of Polymer Science*, Vol. XXXIII, No. 126, pp. 503–504 (1958).

Cocatalytic Activity of Some Metal Salts on Vinyl Polymerization with Tributhylboron, I. M. Panayotov, *Comptes rendus de l'Academie bulgare des Scienses*, vol. 14, No. 2, pp. 147–150 (1961).

Polymerization with Organoboron Compounds, F. Arimoto, *Journal of Polymer Science: Part A–1*, vol. 4, pp. 275–282 (1966).

On the Existence of a Free–Radical Organoboron Complex in the Polymerization of Methyl Methacrylate, R. Kern and J. Schaefer, *Polymer Letters*, vol. 5, pp. 157–162 (1967).

Vinyl Monomer Polymerization Mechanism in the Presence of Trialkylboranes, J. Grotewold, E. Lissi and A. Villa, *Journal of Polymer Science: Part A–1*, vol. 6, pp. 3157–3162 (1968).

Free–Radical Polymerization of Methyl Methacrylate in the Presence of Trialkylboranes, P. Brindley and R. Pearson, *Polymer Letters*, vol. 6, pp. 831–835 (1968).

Ethylene Polymerization in Presence of Tributylboron G. Kolesnikov and T. Soboleva, *Scientific and Research Publications of the Members of the All Union Chemistry Society Name After Mendilev*, vol. 2, p. 663 (1957).

Studies on Dental Self–Curing Resins (II), S. Fujisawa, Y. Imai and E. Masuhara, *Reports of the Institute for Medical & Dental Engineering*, vol. 3, pp. 64–71 (1969).

Free–Radical Copolymerization of 1,2–Dichloroethylenes, Evidence for Chain Transfer by Chlorine Atom Elimination, T. Dawson, R. Lundberg and F. Welch, *Journal of Polymer Science: Part A–1*, vol. 7, pp. 173–181 (1969).

Mechanism of Vinyl Monomer Polymerization in the Presence of Trialkylboranes and Inhibitors, E. Aranchibia et al., *Journal of Polymer Science: Part A–1*, vol. 7, pp. 3430–3433 (1969).

Polymerization of Methyl Methacrylate by Trialkylborane–Pyridine System, K. Kojima et al., *Polymer Letters*, vol. 8, pp. 541–547 (1970).

Polymerization Initiated by Triethylborane–Peroxide Mixtures, E. Abuin et al., *Polymer Letters*, vol. 7, pp. 515–518 (1970).

Polymerization of Methyl Methacrylate by Co–ordination Compounds of Tri–n–butylborane with Some Electron–donating Compounds, Kojima et al., *Research Report of the Chiba University faculty of Engineering*, vol. 22, No. 41, pp. 47–55.

Polymerization of Methyl Methacrylate Initiated by Tri–n––butylborane–Organic Halide Systems, M. Yoshikuni, M. Asami, S. Iwabuchi and K. Kojima, *Journal of Polymer Science*, vol. 11, pp. 3115–3124 (1973).

Polymerization of Methyl Methacrylate Initiated by Tributylborane–Pyridine System, Kojima et al., *Journal of the Japanese Chemical Society*, No. 11, pp. 2165–2171 (1972).

The Copolymerization of Vinylhydroquinone and Acrylonitril by Tri–n–butylborane, S. Iwabuchi, M. Ueda, M. Kobayashi and K. Kojima, *Polymer Journal* pp. 185–190 (1974).

Free Radical Polymerization in the Presence of Triethylborane, E. Abuin, J. Cornejo and E. Lissi, *European Polymer Journal*, vol. 11, pp. 779–782 (1975).

Polymerization of Methyl Methacrylate by tri–n–butylborane in the presence of amino acid esters, K. Kojima, S. Iwabuchi, Y. Moriya and M. Yoshikuni, *Polymer*, vol. 16, pp. 601–604 (1975).

Analysis of Mechanism of Radical Formation Resulted from the Initiator System of Triethylboron and Oxygen by Spin Trapping Technique, Sato et al., *Journal of the Japanese Chemical Society*, No. 6, pp. 1080–1084 (1975).

Development of Adhesive Pit and Fissure Sealants Using a MMA Resin Initiated by a Tri–n—butyl Borane Derivative, N. Nakabayashi and E. Masuhara, *Journal of Biomedical Materials Research*, vol. 12, pp. 149–165 (1978).

Vinyl Acetate Polymerization Initiated by Alkylborane–oxidizer–type Systems, S. Ivanchev, L. Shumnyi and V. Konovalenko, *Polymer Science U.S.S.R.*, vol. 22, No. 12, pp. 8000–8006 (1980).

Preparation of Hard Tissue Compatible Materials: Dental Polymers, N. Nakabayashi and E. Masuhara, *Biomedical Polymers*, pp. 85–111 (1980).

Mechanism of Initiation of Polymerization of Vinyl Monomers by Means of the Trialkylborane–Acid Systems, S. Ivanchev and L. Shumnyi, translated from *Doklady Akademii Nauk SSSR*, vol. 270, No. 5, pp. 1127–1129 (1983).

Effect of Organic Bases on initiating Properties in the System Boronalkylelemental Organic Peroixde During Vinylchloride Polymerization, T. Guzanova Master Thesis of the Fifth (graduate) year student, Ministry of High and Secondary Special Education Russia, Gorky State University (1983).

Application of Spin Trapping Technque to Radical Polymerization, 20, T. Sato, N. Fukumura and T. Otsu, *Makromol. Chem.*, 184, pp. 431–442 (1983).

Importance of Polymerization Initiator Systems and Interfacial Initiation of Polymerization in Adhesive Bonding of Resin to Dentin, Y. Imai, Y. Kadoma, K. Kojima, T. Akimoto, K. Ikakura and T. Ohta, *J. Dent. Res.*, vol. 70, No. 7, pp. 1088–1091 (1991).

Vibrational Analysis by Raman Spectroscopy of the Interface Between Dental Adhesive Resin and Dentin, M. Suzuki, H. Kato and S. Wakumoto, *J. Dent. Res.*, vol. 70, No. 7, pp. 1092–1097 (1991).

Laser–Raman Spectroscopic Study of the Adhesive Interface Between 4–MET/MMA–TBB Resin and Hydroxyapatite or Bovine Enamel, M. Ozaki, M. Suzuki, K. Itoh and S. Wakumoto, *Dental Materials Journal*, vol. 10, No. 2, pp. 105–120 (1991).

Polymerization of Some Vinyl Monomers on triisobutylboron–Containing Radical Initiators in the Presence of Hydroquinone and Benzoquinone, V. Dodonov and D. Grishin, *High Molecular Compounds*, vol. 35, No. 3, pp. 137–141 (1993).

Synthesis of PP–g–PMMA, PP–g–PVA and PP–g–PCL Copolymers, D. Rhubright and T. Chung, American Chemical Society, Division of Polymer Chemistry, Papers Presented at the Chicago, Illinois Meeting, vol. 34, No. 2, pp. 560–561 (1993).

Functionalized and Grafted Polyolefin Copolymers Prepared by Tansition Metal Catalysts and Borane Monomers, T. Chung, *Polymer Reprints*, vol. 35, No. 1, pp. 674–675 (1994).
Photochemical Modification of Fluorocargon Resin Surface to Adhere with Epoxy Resin, M. Okoshi, T. Miyokawa, H. Kashiura and M. Murahara, *Mat. Res. Soc. Symp. Proc.*, vol. 334, pp. 356–371 (1994).
Chemical Abstract No. 88532r, *Chemical Abstracts*, vol. 73, 1970.
Chemical Abstract No. 134385q, *Chemical Abstracts*, vol. 80, 1974.

ORGANOBORANE POLYOXYALKYLENEPOLYAMINE COMPLEXES AND ADHESIVE COMPOSITIONS MADE THEREWITH

This is a division of application Ser. No. 08/422,429 filed Apr. 14, 1995 now U.S. Pat. No. 5,621,143.

BACKGROUND OF THE INVENTION

1. Field of the Invention

This invention relates generally to organoborane polyamine complexes and, more specifically, to such complexes that incorporate polyoxyalkylenepolyamines. The invention further relates to the use of these complexes in systems for initiating the polymerization of acrylic monomers, as well as acrylic adhesive compositions made therewith. The adhesive compositions have excellent adhesion to a variety of substrates, especially low surface energy polymers.

2. Description of the Related Art

Organoboranes such as tributylborane and triethylborane have been reported to initiate and catalyze the polymerization of vinyl monomers (see, for example, G. S. Kolesnikov et al., Bull. Acad. Sci. USSR, Div. Chem. Sci. 1957, p. 653; J. Furakawa et al., Journal of Polymer Science, volume 26, issue 113, p. 234, 1957; and J. Furakawa et al., Journal of Polymer Science, volume 28, issue 116, 1958). The organoborane compounds of the type described in these references are known to be quite pyrophoric in air which complicates facile use.

Chemical Abstracts No. 134385q (volume 80, 1974) "Bonding Polyolefin or Vinyl Polymers" reports that a mixture of 10 parts methyl methacrylate, 0.2 part tributylborane, and 10 parts poly(methylmethacrylate) was used to bond polyethylene, polypropylene and poly(vinyl acetate) rods.

U.S. Pat. No. 3,275,611 to E. H. Mottus et al. discloses a process for polymerizing olefinic compounds with a catalyst comprising an organoboron compound, a peroxygen compound, and an amine. The organoboron compound and the amine may be added to the reaction mixture separately or they may be added as a preformed complex. The latter approach reportedly has the advantage of making the boron compound more easily handled, especially for certain boron compounds that tend to be pyrophoric in air but which are not pyrophoric when complexed. Especially useful boron catalysts are said to have the following general formulas: $R_3B$, $RB(OR)_2$, $R_2B(OR)$, $R_2BOBR_2$, $R_2BX$, and $R_2BH$, where R is preferably an alkyl radical having from 1 to 10 or more carbon atoms, and X is a halogen. Various amine complexing agents are mentioned although pyridine, aniline, toluidine, dimethylbenzylamine, and nicotine are used in the examples.

While Mottus et al. refer to polymerizing methacrylate monomers, there is no indication that the resulting polymers are useful as adhesives. Various acids are mentioned as monomers that may be polymerized but there is no indication that an acid is a component of the polymerization initiator system.

British Patent Specification No. 1,113,722 "Aerobically Polymerisable Compositions," published May 15, 1968 discloses the polymerization of acrylate monomers through the use of a free-radical catalyst (e.g., peroxides) and triarylborane complexes having the general formula $(R)_3B$—Am wherein R is an aryl radical having from 6 to 12 carbon atoms and Am is an amine that can be selected from various classes such as alkylamines, cycloalklyamines, aralklyamines, polyamines (e.g., alkylene diamines and triamines), and heterocyclic amines. The polymerization is activated by heat or the addition of an acid. The resulting compositions are reportedly useful as adhesives.

Chemical Abstracts No. 88532r (volume 73, 1970) "Dental Self-curing Resin" and the full text paper to which it refers report that tributylborane can be made stable in air by complexing it with ammonia or certain amines (e.g., aniline, n-butylamine, piperidine, ethylenediamine) at a mole ratio of one and that the tributylborane can be reactivated with an amine acceptor such as an isocyanate, an acid chloride, a sulfonyl chloride, or anhydrous acetic acid. As a result, the complex can be used to polymerize blends of methyl methacrylate and poly(methylmethacrylate) to provide a dental adhesive. Tributylborane-ethylenediamine complexes and triethylborane-ammonia complexes, each with p-toluenesulfonyl chloride as the amine acceptor, are specifically mentioned.

A series of patents issued to Skoultchi and Skoultchi et al. (U.S. Pat. Nos. 5,106,928, 5,143,884, 5,286,821, 5,310,835, and 5,376,746) disclose a two part initiator system that is reportedly useful in acrylic adhesive compositions, especially elastomeric acrylic adhesives. The first part of this two part system includes a stable organoborane amine complex and the second part includes a destabilizer or activator such as an organic acid or an aldehyde. The organoborane compound of the complex has the general formula:

where R, $R_1$ and $R_2$ are either alkyl groups having 1 to 10 carbon atoms or phenyl groups. Useful amines include n-octylamine, 1,6-diaminohexane, diethylamine, dibutylamine, diethylenetriamine, dipropylenediamine, 1,3-propylenediamine, and 1,2-propylenediamine.

The adhesive compositions are reportedly particularly useful in structural and semi-structural applications such as speaker magnets, metal-metal bonding, (automotive) glass-metal bonding, glass-glass bonding, circuit board component bonding, selected plastic to metal, glass, wood, etc. bonding, and electric motor magnets. Those plastics that may be bonded are not further described.

An efficient, effective means for adhesively bonding low surface energy plastic substrates such as polyethylene, polypropylene and polytetrafluoroethylene (e.g., TEFLON) has long been sought. The difficulties in adhesively bonding these materials are well known. See, for example, "Adhesion Problems at Polymer Surfaces" by D. M. Brewis that appeared in *Progress in Rubber and Plastic Technology*, volume 1, page 1 (1985). The conventional approaches typically function by: (1) increasing the surface energy of the substrate (to more closely match the surface energies of the substrate and the adhesive thereby promoting better wetting of the substrate by the adhesive) and/or (2) eliminating additives and low molecular weight polymer fractions in the substrate that can migrate to the substrate surface and adversely affect adhesion by forming a weak boundary layer.

As a result, the conventional approaches often use complex and costly substrate surface preparation techniques such as flame treatment, corona discharge, plasma treatment, oxidation by ozone or oxidizing acids, and sputter etching. Alternatively, the substrate surface may be primed by coating it with a high surface energy material. However, to achieve adequate adhesion of the primer, it may be necessary to first use the surface preparation techniques described above. All of these techniques are well known, as reported in *Treatise on Adhesion and Adhesives* (J. D. Minford, editor, Marcel Dekker, 1991, New York, volume 7, pages 333 to 435). The known approaches are frequently customized for use with specific substrates. As a result, they may not be useful for bonding low surface energy plastic substrates generally.

Moreover, the complexity and cost of the presently known approaches do not render them particularly suitable for use by the retail consumer (e.g., home repairs, do-it-yourselfers, etc.) or in low volume operations. One vexing problem is the repair of many inexpensive everyday household articles that are made of polyethylene, polypropylene or polystyrene such as trash baskets, laundry baskets and toys.

Consequently, there has been a considerable and long felt need for a simple, easy to use adhesive that can readily bond a wide variety of substrates, especially low surface energy materials, such as polyethylene, polypropylene and polytetrafluoroethylene, without requiring complicated surface preparation, priming and the like. It would also be considered useful for the adhesive to be able to bond a wide variety of diverse surfaces, including metals.

While an adhesive that can bond low surface energy plastics is certainly advantageous, the commercial utility of such an adhesive would be enhanced if the components thereof could be combined in a convenient mix ratio. This would permit facile application of the adhesive using conventional adhesive dispensers without the need for laborious hand weighing and mixing of the different components. However, the convenient mix ratio should not come at the expense of significantly reduced storage stability or performance. Thus, there is not only a need for an adhesive that can bond low surface energy plastics, but a need for such an adhesive that can be readily blended in a convenient mix ratio without a material reduction in storage stability or performance.

SUMMARY OF THE INVENTION

The invention relates to organoborane polyamine complexes and, more particularly, to such complexes that include polyoxyalkylenepolyamine. The complexes can be used in systems that initiate the polymerization of acrylic monomer to yield acrylic adhesive compositions. The acrylic adhesive compositions have excellent adhesion to a wide variety of substrates but are especially useful for bonding low surface energy plastics (e.g., polyethylene, polypropylene, polytetrafluoroethylene, etc.) that, heretofore, have been bonded using complex and costly surface preparation techniques.

In general, complexes of the invention comprise organoborane and polyoxyalkylenepolyamine. The organoborane polyamine complexes have the general structure:

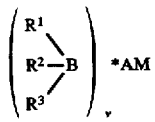

wherein Am is polyoxyalkylenepolyamine and has a structure selected from the group consisting of

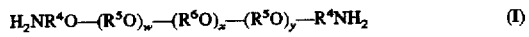

and

In this structure, $R^1$ is preferably an alkyl group having 1 to 10 carbon atoms, and $R^2$ and $R^3$ are independently selected from alkyl groups having 1 to 10 carbon atoms and phenyl-containing groups. More preferably, $R^1$, $R^2$ and $R^3$ are alkyl groups having 1 to 5 carbon atoms. Most preferably, $R^1$, $R^2$ and $R^3$ are the same.

$R^4$, $R^5$ and $R^6$ are preferably alkylene groups having 1 to 10 carbon atoms and which may be the same or which may be different. More preferably, $R^4$ is an alkyl group having 2 to 4 carbon atoms, $R^5$ is an alkyl group of 2 or 3 carbon atoms, and $R^6$ is an alkyl group of 2 or 3 carbon atoms. $R^7$ is a residue of a poylol.

The value of w is $\geq 1$ (more preferably about 1 to 150, and most preferably about 1 to 20). The value of x and y are $\geq 0$. The value of z is >2 (more preferably 3 or 4). The values for w, x, y and z are preferentially selected such that the complex is a liquid at room temperature. Consequently, the molecular weight of the polyoxyalkylenepolyamine is less than about 5,000, more preferably about 1,000 or less, and most preferably about 250 to 1,000.

The value of v is selected so as to provide an effective ratio of nitrogen atoms to boron atoms in the complex. In complexes employing polyoxyalkylenepolyamine (I), the value of v may broadly vary over the range of about 0.1 to 2. In complexes employing polyoxyalkylenepolyamine (II), the value of v may broadly vary over the range of about 0.1 to z. The ratio of nitrogen atoms to boron atoms in the complex should be about 1:1 to 4:1, preferably about 1:1 to 2:1, more preferably about 1:1 to 1.5:1, and most preferably about 1:1.

Organoborane polyamine complexes of the invention can be used in systems that are capable of initiating the polymerization of an acrylic monomer. In addition to organoborane polyamine complexes such as those described above, these systems further comprise an effective amount of a compound that is reactive with amine for liberating the organoborane. A wide variety of amine reactive compounds may be used including isocyanates, acids, acid chlorides, sulfonyl chlorides, and aldehydes. Useful acids include Lewis acids and Bronsted acids, although acrylic acid and methacrylic acid are preferred. The amount of amine reactive compound is preferentially stoichiometric with the equivalents of amine but larger amounts may be used, for example, twice stoichiometric. Where an acid provides the amine reactive compound, a useful amount is in the range of about 100 to 350 mole %, more preferably about 150 to 250 mole %.

Consequently, the invention also relates to a polymerizable acrylic composition that comprises at least one acrylic monomer, an effective amount of an organoborane polyamine complex of the invention, and an effective amount of a compound that is reactive with amine (such as those described above) for liberating the organoborane to initiate polymerization of the at least one acrylic monomer.

A wide variety of acrylic monomers may be used but those which are preferred include monofunctional acrylate ester, monofunctional methacrylate ester, substituted derivatives of the foregoing, and blends of the foregoing. Methacrylate esters are especially useful, particularly desirable examples of which include methyl methacrylate, ethyl methacrylate, methoxy ethyl methacrylate, hydroxyethyl methacrylate, hydroxypropyl methacrylate, cyclohexyl methacrylate, tetrahydrofurfuryl methacrylate, and blends thereof. Blends of alkyl methacrylate (e.g., methyl methacrylate) and alkyl acrylate (especially those in which the alkyl group has from 4 to 10 carbon atoms, e.g., butyl acrylate) are also quite useful.

Acrylic compositions of the invention are uniquely useful in providing adhesives, and adhesive compositions of the invention provide excellent adhesion to low surface energy polymeric or plastic substrates that historically have been very difficult to bond. Adhesion to low surface energy polymeric substrates is enhanced when the adhesive composition comprises about 0.03 to 1.5 weight % boron, more preferably about 0.1 to 0.3 weight % boron.

Consequently, in another aspect, the invention relates to a composite article comprising a first substrate, and a second substrate bonded to the first substrate by an acrylic adhesive composition according to the invention. Either or both substrates may be a low surface energy polymer or plastic such as polyethylene, polypropylene or polytetrafluoroethylene.

In another aspect, the invention relates to a method of initiating the polymerization of an acrylic monomer, the method comprising the steps of providing at least one acrylic monomer, blending the at least one acrylic monomer with a polymerization initiator system according to the invention, and initiating polymerization of the at least one acrylic monomer.

The invention further relates to a method of bonding a low surface energy polymer to a substrate. The method comprises the steps of providing a low surface energy polymer, providing substrate, providing an adhesive composition according to the invention, applying the adhesive composition to either the low surface energy polymer or the substrate, joining the low surface energy polymer and the substrate with the adhesive composition therebetween, and permitting the adhesive composition to cure to adhesively bond the low surface energy polymer and the substrate.

DETAILED DESCRIPTION OF THE PREFERRED EMBODIMENTS

In a broad aspect, this invention relates to organoborane polyamine complexes, particularly those complexes that are made from polyoxyalkylenepolyamine. The complexes are especially useful in providing systems for initiating the polymerization of acrylic monomer. Acrylic adhesives can be produced using the organoborane polyamine complexes of the invention. The acrylic adhesives can bond a wide variety of substrates, but provide exceptionally good adhesion to low surface energy plastic substrates (e.g., polyethylene, polypropylene, polytetrafluoroethylene, etc.) that, heretofore, have been bonded using complex and costly surface preparation techniques.

The complexes of the invention are complexes of organoborane and polyoxyalkylenepolyamine. They preferably have the following general structure:

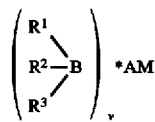

where $R^1$ is an alkyl group having 1 to 10 carbon atoms, and $R^2$ and $R^3$ are independently selected from alkyl groups having 1 to 10 carbon atoms and phenyl-containing groups. More preferably, $R^1$, $R^2$ and $R^3$ are alkyl groups having 1 to 5 carbon atoms such as methyl, ethyl, propyl, iso-propyl, n-butyl, iso-butyl, and pentyl. In general, shorter carbon chain lengths are preferred for the $R^1$, $R^2$ and $R^3$ groups as this promotes enhanced stability of the complex in air. Smaller, less bulky substituents are also preferred as larger, more bulky groups may negatively affect the adhesion provided by adhesives made therewith. By "independently selected" it is meant that $R^2$ and $R^3$ may be the same or that they may be different. $R^1$ may be the same as $R^2$ or $R^3$, or it may be different. Preferably $R^1$, $R^2$ and $R^3$ are the same. Most preferred are complexes in which $R^1$, $R^2$ and $R^3$ are each ethyl groups.

"Am" represents the polyoxyalkylenepolyamine portion of the complex and may be selected from the following structures:

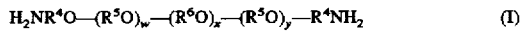

(i.e., polyoxyalkylene diamines) or

Blends of different polyoxyalkylenepolyamines may also be used. $R^4$, $R^5$ and $R^6$ are alkylene groups having 1 to 10 carbon atoms and may be the same or may be different. Preferably, $R^4$ is an alkyl group having 2 to 4 carbon atoms such as ethyl, n-propyl, iso-propyl, n-butyl or iso-butyl. Preferably, $R^5$ is an alkyl group having 2 or 3 carbon atoms such as ethyl, n-propyl or iso-propyl. Preferably, $R^6$ is an alkyl group having 2 or 3 carbon atoms such as ethyl, n-propyl or isopropyl. $R^7$ is the residue of a polyol used to prepare the polyoxyalkylenepolyamine(i.e., the organic structure that remains if the hydroxyl groups are removed). $R^7$ may be branched or linear, saturated or unsaturated, and substituted or unsubstituted (although any substituents should not interfere with oxyalkylation reactions). Residues that are branched, saturated and/or unsubstituted are preferred.

The value of w is $\geq 1$, more preferably about 1 to 150, and most preferably about 1 to 20. Structures in which w is 2, 3 or 4 are useful too. The value of x and y are both $\geq 0$. The value of z is >2, more preferably 3 or 4 (so as to provide, respectively, polyoxyalkylene triamines and tetraamines). The selection of values for w, x, y and z influences the physical form of the complex and the molecular weight of the polyoxyalkylenepolyamine. It is preferred that the values of w, x, y and z be chosen such that the resulting complex is a liquid at room temperature as this simplifies handling and mixing thereof. Usually, the polyoxyalkylenepolyamine is itself a liquid. Lower molecular weight polyoxyalkylenepolyamines are also preferred in order to promote solubility of the complex in compositions made therewith and to enhance the performance of ultimate compositions that incorporate the complex. Molecular weights of less than about 5,000 may be used, although molecular weights of about 1,000 or less are more preferred, and molecular weights of about 250 to 1,000 are most preferred.

Examples of particularly preferred polyoxyalkylenepolyamines include polyethyleneoxidediamine, polypropyleneoxidediamine, polypropyleneoxidetriamine, diethyleneglycolpropylenediamine, triethyleneglycolpropylenediamine, polytetramethyleneoxidediamine, polyethyleneoxide-co-polypropyleneoxidediamine, and polyethyleneoxide-co-polyproyleneoxidetriamine.

Examples of suitable commercially available polyoxyalkylenepolyamines include various JEFFAMINES from Huntsman Chemical Company such as the D, ED, and EDR series diamines (e.g., D-400, D-2000, D-5000, ED-600, ED-900, ED-2001, and EDR-148), and the T series triamines (e.g., T-403), as well as H221 from Union Carbide Company.

The value of v is selected so as to provide an effective ratio of nitrogen atoms to boron atoms in the complex, as explained more fully hereinbelow. For polyoxyalkylenepolyamine I, the value of v is preferably in the range of about 0.1 to 2. For polyoxyalkylenepolyamine II, the value of v is preferably in the range of about 0.1 to z, the value of z for any particular complex providing the upper boundary of the preferred range for v. For polyoxyalkylenepolyamine II, the value of v is preferably 3 or 4 when z is, respectively, 3 or 4.

Highly preferred organoborane polyamine complexes according to the invention include triethylborane complexed with any of the "particularly preferred" polyoxyalkylenepolyamines mentioned above.

The nitrogen atom to boron atom ratio in the complex is broadly about 1:1 to 4:1. Preferably, however, the ratio is about 1:1 to 2:1, more preferably about 1:1 to 1.5:1, and most preferably about 1:1. A nitrogen atom to boron atom ratio of less than 1:1 leaves free organoborane, a material that tends to be pyrophoric. At nitrogen atom to boron atom ratios in excess of 2:1, the practical utility of the complex in, for example, an adhesive system diminishes as the amount of complex that must be employed to generate a useful adhesive becomes larger. In addition, at high nitrogen atom to boron atom ratios, the amount of agent that must be added to react with the polyamine so as to liberate organoborane (to initiate polymerization) also becomes larger. The additional reactants could complicate the adhesive system.

The organoborane polyamine complex is employed in an effective amount, which is an amount large enough to permit polymerization to readily occur to obtain a polymer (preferably, an acrylic polymer) of high enough molecular weight for the desired end use. If the amount of organoborane polyamine complex is too low, then the polymerization may be incomplete or, in the case of adhesives, the resulting composition may have poor adhesion. On the other hand, if the amount of organoborane polyamine complex is too high, then the polymerization may proceed too rapidly to allow for effective mixing and use of the resulting composition. Large amounts of complex could also lead to the generation of large volumes of borane, which, in the case of an adhesive, could weaken the bondline. The useful rate of polymerization will depend in part on the method of applying the composition to a substrate. Thus, a faster rate of polymerization may be accommodated by using a high speed automated industrial adhesive applicator rather than by applying the composition with a hand applicator or by manually mixing the composition.

Within these parameters, and in the particular case of an adhesive, an effective amount of the organoborane polyamine complex is an amount that preferably provides about 0.03 to 1.5 weight % boron, based on the total weight of the adhesive composition, more preferably about 0.1 to 0.3 weight % boron.

The weight % of boron in a composition is equal to the following:

$$\frac{\text{(weight of complex in the composition)} \times \text{(weight \% of boron in the complex)}}{\text{(Total weight of composition)}}$$

The organoborane polyamine complexes may be readily prepared using known techniques. Typically, the polyamine is combined with the organoborane in an inert atmosphere with slow stirring. An exotherm is often observed and cooling of the mixture is, therefore, recommended. If the ingredients have a high vapor pressure, it is desirable to keep the reaction temperature below about 70° to 80° C. Once the materials have been well mixed the complex is permitted to cool to room temperature. No special storage conditions are required although it is preferred that the complex be kept in a capped vessel in a cool, dark location. Advantageously, the complexes of the invention can be prepared in the absence of organic solvents that would later have to be removed, although they could be prepared in solvent if so desired. Solvents used in the preparation of the complexes should, preferably, be ones that do not coordinate amines, for example, tetrahydrofuran or hexane.

Advantageously, the preferred organoborane polyamine complexes of the invention are air stable. By "air stable" it is meant that when the complexes are stored in a capped vessel at room temperature (about 20° to 22° C.) and under otherwise ambient conditions (i.e., not under a vacuum and not in an inert atmosphere), the complexes remain useful as polymerization initiators for at least about two weeks, although the complexes may be readily stored under these conditions for many months and up to a year or more. By "air stable" it is also meant that the complexes are not pyrophoric, as explained more fully hereinbelow. The air stability of the complex is enhanced when the complex is a crystalline material. However, the complexes of the invention are air stable for at least six months even when they are liquids. Liquid complexes are easier to handle and mix than are crystalline complexes.

As noted above, the organoborane polyamine complexes of the invention are especially useful as polymerization initiators, in particular, for initiating the polymerization of acrylic monomers. In such cases, the organoborane polyamine complexes form one component of a polymerization initiator system that comprises and, more preferably, consists essentially of an effective amount of the organoborane polyamine complex and an effective amount of a compound that is reactive with amine for liberating organoborane so as to initiate polymerization.

The amine reactive compound liberates organoborane by reacting with the polyamine, thereby removing the organoborane from chemical attachment with the polyamine. A wide variety of materials may be used to provide the amine reactive compound. Desirable amine reactive compounds are those materials that can readily form reaction products with amines at or below (and, more preferably, at) room temperature (about 20° to 22° C.) so as to provide a composition such as an adhesive that can be easily used and cured under ambient conditions. General classes of such compounds include isocyanate, acid chloride, sulfonyl chloride, aldehyde, and the like. Particular examples of compounds falling within these general classes include toluene diisocyanate, benzaldehyde, and methacryloyl chloride.

The amine reactive compound is employed in an effective amount; that is, an amount effective to promote polymerization by liberating organoborane from the complex but without materially adversely affecting the properties of the ultimate polymerized composition. Larger amounts of amine reactive compound may permit the polymerization to proceed too quickly and, in the case of adhesives, the resulting materials may demonstrate inadequate adhesion to low energy surfaces. Undesirable side reactions that adversely affect the performance properties of the polymerized composition, or an undesirably high level of extractables in the polymerized composition may also result from using large amounts of amine reactive compound. On the other hand, an excess of certain amine reactive compounds may promote adhesion to higher energy surfaces. If small amounts of amine reactive compound are employed, the rate of polymerization may be too slow and the monomers that are being polymerized may not adequately increase in molecular weight. However, a reduced amount of amine reactive compound may be helpful in slowing the rate of polymerization if it is otherwise too fast.

Within these parameters, the amine reactive compound may be provided in an amount wherein the number of equivalents of amine reactive groups is as much as twice stoichiometric with the number of amine groups in the organoborane polyamine complex. However, it is much more preferred that the number of equivalents of amine reactive groups be stoichiometric with the number of amine groups in the organoborane polyamine complex.

Acids may also be used as the amine reactive compound. Any acid that can liberate the organoborane by salting the polyamine group may be employed. Useful acids include Lewis acids (e.g., SnCl$_4$, TiCl$_4$ and the like) and Bronsted acids such as those having the general formula R$^8$—COOH, where R$^8$ is hydrogen, an alkenyl group of 1 to 8 and preferably 1 to 4 carbon atoms, or an aryl group of 6 to 10, preferably 6 to 8 carbon atoms. The alkenyl groups may comprise a straight chain or they may be branched. They may be saturated or unsaturated. The aryl groups may contain substituents such as alkyl, alkoxy or halogen moieties. Illustrative acids of this type include acrylic acid, methacrylic acid, acetic acid, benzoic acid, and p-methoxybenzoic acid. Other useful Bronsted acids include HCl, H$_2$SO$_4$, H$_3$PO$_4$ and the like. Acrylic acid and methacrylic acid are preferred.

Somewhat different formulating is preferred with acids which, preferably, are provided in an amount of about 100 to 350 mole % based on the number of equivalents of amine groups, moieties or functionality present in the complex, more preferably about 150 to 250 mole %.

The organoborane polyamine complex initiator systems of the invention are especially useful in polymerizing acrylic monomers, particularly for making polymerizable acrylic adhesives. By "acrylic monomer" is meant polymerizable monomers having one or more acrylic or substituted acrylic moieties, chemical groups or functionality; that is, groups having the general structure

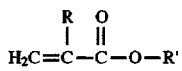

wherein R is hydrogen or an organic radical and R' is an organic radical. Where R and R' are organic radicals, they may be the same or they, may be different. Blends of acrylic monomers may also be used. The polymerizable acrylic monomer may be monofunctional, polyfunctional or a combination thereof.

The most useful monomers are monofunctional acrylate and methacrylate esters and substituted derivatives thereof such as hydroxy, amide, cyano, chloro, and silane derivatives as well as blends of substituted and unsubstituted monofunctional acrylate and methacrylate esters. Particularly preferred monomers include lower molecular weight methacrylate esters such as methyl methacrylate, ethyl methacrylate, methoxy ethyl methacrylate, hydroxyethyl methacrylate, hydroxypropyl methacrylate, cyclohexyl methacrylate, tetrahydrofurfuryl methacrylate, and blends thereof.

Both acrylate esters and higher molecular weight methacrylate esters are less preferred for use alone, but can be especially usefully employed as modifying monomers with predominating amounts of lower molecular weight methacrylate esters so as to, for example, enhance the softness or flexibility of the ultimate composition. Examples of such acrylate esters and higher molecular weight methacrylate esters include methyl acrylate, ethyl acrylate, isobornyl methacrylate, hydroxypropyl acrylate, butyl acrylate, n-octyl acrylate, 2-ethylhexyl acrylate, 2-ethylhexyl methacrylate, decylmethacrylate, dodecyl methacrylate, tert-butyl methacrylate, acrylamide, N-methyl acrylamide, diacetone acrylamide, N-tert-butyl acrylamide, N-tert-octyl acrylamide, N-butoxyacrylamide, gamma-methacryloxypropyl trimethoxysilane, 2-cyanoethyl acrylate, 3-cyanopropyl acrylate, tetrahydrofurfuryl chloroacrylate, glycidyl acrylate, glycidyl methacrylate, and the like. Dimethylaminoethyl acrylate and dimethylamino methacrylate may also be used as modifying agents although the additional amine functionality may require a larger amount of amine reactive compound.

Particularly preferred are blends of any of the lower molecular weight alkyl methacrylate esters described above with alkyl acrylates having 4 to 10 carbon atoms in the alkyl group, such as blends of methyl methacrylate and butylacrylate. Polymerizable compositions of this type may broadly comprise, based on the total weight of the composition, about 2 to 40 wt. % of the alkyl acrylate and, correspondingly, about 60 to 98 wt. % of the alkyl methacrylate.

Another class of polymerizable monomers that are especially useful as modifiers, such as for improving the creep resistance or temperature resistance of the ultimate composition, corresponds to the general formula:

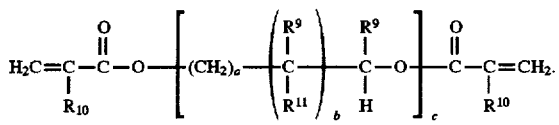

R$^9$ may be selected from the group consisting of hydrogen methyl, ethyl, —CH$_2$OH, and

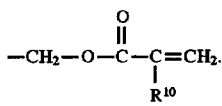

R$^{10}$ may be selected from the group consisting of chlorine, methyl and ethyl. R$^{11}$ may be selected from the group consisting of hydrogen, hydroxy, and

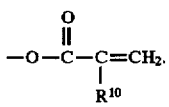

The value of a is an integer greater than or equal to 1, more preferably, from 1 to about 8, and most preferably from 1 to 4. The integral value of b is greater than or equal to 1, more preferably, from 1 to about 20. The value of c is 0 or 1.

Other acrylic monomers useful with the polymerization initiator systems, especially as modifying monomers, include ethylene glycol dimethacrylate, ethylene glycol diacrylate, polyethylene glycol diacrylate, tetraethylene glycol dimethacrylate, diglycerol diacrylate, diethylene glycol dimethacrylate, pentaerythritol triacrylate, trimethylolpropane trimethacrylate, as well as other polyether diacrylates and dimethacrylates.

Other polymerizable monomers that are useful in the invention, particularly as modifying monomers, have the general formula:

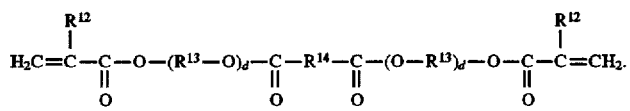

$R^{12}$ may be hydrogen, chlorine, methyl or ethyl; $R^{13}$ may be an alkylene group with 2 to 6 carbon atoms; and $R_{14}$ is $(CH_2)_e$ in which e is an integer of 0 to 8, or one of the following:

acrylate esters of bisphenol type compounds. These monomers may be described by the following formula:

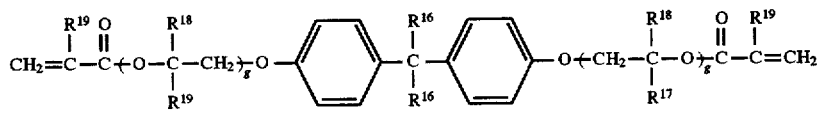

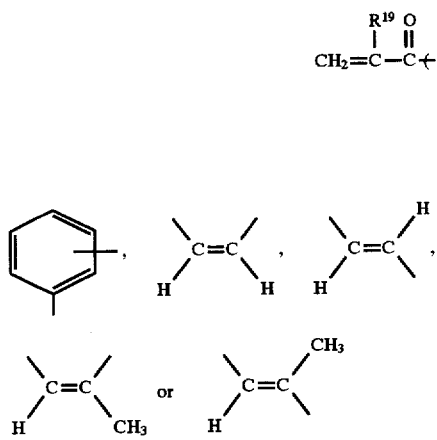

the phenyl group being substitutable at any one of the ortho, meta or para positions. The value of d is an integer of 1 to 4.

Typical monomers of this class include dimethacrylate of bis(ethylene glycol) adipate, dimethacrylate of bis(ethylene glycol) maleate, dimethacrylate of bis(ethylene glycol) phthalate, dimethacrylate of bis(tetraethylene glycol) phthalate, dimethacrylate of bis(tetraethylene glycol) sebacate, dimethacrylates of bis(tetraethylene glycol) maleate, and the diacrylates and chloroacrylates corresponding to the dimethacrylates, and the like.

Also useful as modifying agents are monomers that are isocyanate-hydroxyacrylate or isocyanate-aminoacrylate reaction products. These may be characterized as acrylate terminated polyurethanes and polyureides or polyureas. Such monomers have the following general formula:

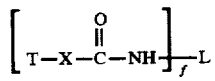

where X is selected from the group consisting of —O— and

$R^{15}$ is selected from the group consisting of hydrogen and lower alkyl groups (e.g., 1 to 7 carbon atoms). T is the organic residue of an active hydrogen-containing acrylic ester, the active hydrogen having been removed and the ester being hydroxy or amino substituted on the alkyl portion thereof (including the methyl, ethyl and chlorine homologs). The integral value of f is from 1 to 6. L is a mono- or polyvalent organic radical selected from the group consisting of alkyl, alkylene, alkenyl, cycloalkyl, cycloalkylene, aryl, aralkyl, alkaryl, poly(oxyalkylene), poly (carboalkoxyalkylene), and heterocyclic radicals, both substituted and unsubstituted.

Typical monomers of this class include the reaction product of mono- or polyisocyanates, for example, toluene diisocyanate, with an acrylate ester containing a hydroxy or an amino group in the non-acrylate portion thereof, for example, hydroxyethyl methacrylate.

Still another class of modifying monomers useful in the present invention are the mono- and polyacrylate and methwhere $R^{16}$ is methyl, ethyl, carboxyalkyl or hydrogen; $R^{17}$ is hydrogen, methyl or ethyl; $R^{18}$ is hydrogen, methyl or hydroxyl; $R^{19}$ is hydrogen, chlorine, methyl or ethyl; and g is an integer having a value of 0 to 8. Representative monomers of the above-described class include dimethacrylate and diacrylate esters of 4,4'-bis-hydroxyethoxy-bisphenol A, dimethacrylate and diacrylate esters of bisphenol A, etc.

The compositions may further comprise a variety of optional additives. One particularly useful additive is a thickener such as a medium (e.g., about 100,000) molecular weight polymethyl methacrylate which may be incorporated in an amount of about 10 to 40 weight %, based on the total weight of the composition. Thickeners may be employed to increase the viscosity of the composition to a more easily applied viscous syrup-like consistency.

Another particularly useful additive is an elastomeric material. These materials can improve the fracture toughness of compositions made therewith which can be beneficial when, for example, bonding stiff, high yield strength materials such as metal substrates that do not mechanically absorb energy as easily as other materials, such as flexible polymeric substrates. Such additives can be incorporated in an amount of about 5% to 35% by weight, based on the total weight of the composition.

Useful elastomeric modifiers include chlorinated or chlorosulphonated polyethylenes such as HYPALON 30 (commercially available from E. I. duPont de Nemours and Co., Wilmington Del.). Also useful, and even more preferred, are certain graft copolymer resins such as particles that comprise rubber or rubber-like cores or networks that are surrounded by relatively hard shells, these materials often being referred to as "core-shell" polymers. Most preferred are the acrylonitrile-butadiene-styrene graft copolymers.

In addition to improving the fracture toughness of the composition, core-shell polymers can also impart enhanced spreading and flow properties to the uncured composition. These enhanced properties may be manifested by a reduced tendency for the composition to leave an undesirable "string" upon dispensing from a syringe-type applicator, or sag or slump after having been applied to a vertical surface. Use of more than about 20% of a core-shell polymer additive is desirable for achieving improved sag-slump resistance.

Another useful adjuvant is a crosslinking agent. Crosslinking agents can be used to enhance the solvent resistance of the adhesive bond, although certain compositions of the invention have good solvent resistance even in the absence of externally added crosslinking agents. Typically employed in an amount of about 0.2 to 10 weight % based on the total weight of the composition, useful crosslinkers include the various diacrylates referred to above as possible acrylic modifying monomers as well as other materials. Particular examples of suitable crosslinking agents include ethylene glycol dimethacrylate, ethylene glycol diacrylate, triethyleneglycol dimethacrylate, diethylene glycol bismethacryloxy carbonate, polyethylene glycol diacrylate, tetraethylene glycol dimethacrylate, diglycerol diacrylate, diethylene glycol dimethacrylate, pentaerythritol triacrylate, trimethylolpropane trimethacrylate, as well as other polyether diacrylates and dimethacrylates.

Peroxides may be optionally included (typically in an amount of about 2% by weight or less, based on the total weight of the composition), for example, to adjust the speed at which the compositions polymerize or to complete the polymerization.

Small amounts of inhibitors such as hydroquinone may be used, for example, to prevent or reduce degradation of the acrylic monomers during storage. Inhibitors may be added in an amount that does not materially reduce the rate of polymerization or the ultimate properties of an adhesive or other composition made therewith, typically about 100–10,000 ppm based on the weight of the polymerizable monomers.

Other possible additives include non-reactive colorants, fillers (e.g., carbon black), etc.

The various optional additives are employed in an amount that does not significantly adversely affect the polymerization process or the desired properties of compositions made therewith.

Polymerizable acrylic compositions according to the invention may be used in a wide variety of ways, including as sealants, coatings, and injection molding resins. They may also be used as matrix resins in conjunction with glass and metal fiber mats such as in resin transfer molding operations. They may further be used as encapsulants and potting compounds such as in the manufacture of electrical components, printed circuit boards and the like. Quite desirably, they provide polymerizable acrylic adhesive compositions that can bond a diverse myriad of substrates, including polymers, wood, ceramics, concrete, and primed metals.

Polymerizable acrylic compositions of the invention are especially useful for adhesively bonding low surface energy plastic or polymeric substrates that historically have been very difficult to bond without using complicated surface preparation techniques, priming, etc. By low surface energy substrates is meant materials that have a surface energy of less than 45 mJ/m$^2$, more typically less than 40 mJ/m$^2$ or less than 35 mJ/m$^2$. (The expression "surface energy" is often used synonymously with "critical wetting tension" by others.) Included among such materials are polyethylene, polypropylene, acrylonitrile-butadiene-styrene, polyamide, and fluorinated polymers such as polytetrafluoroethylene (TEFLON) which has a surface energy of less than 20 mJ/m$^2$. Other polymers of somewhat higher surface energy that may be usefully bonded with the compositions of the invention include polycarbonate, polymethylmethacrylate, and polyvinylchloride.

The polymerizable compositions of the invention can be easily used as two-part adhesives. The components of the polymerizable composition are blended as would normally be done when working with such materials. The amine reactive component of the polymerization initiator system is usually included in this blend so as to separate it from the organoborane polyamine complex, thus providing one part of the two-part composition. The organoborane polyamine complex of the polymerization initiator system provides the second part of the composition and is added to the first part shortly before it is desired to use the composition. The complex may be added to the first part directly or it may be predissolved in an appropriate carrier such as a small amount of methyl methacrylate.

While a nitrogen atom to boron atom ratio of about 1:1 in the organoborane polyamine complex is preferred, it is desirable to store such complexes apart from the monomers to inhibit premature polymerization of the monomers. Complexes in which the nitrogen atom to boron atom ratio is greater than 1:1 may be sufficiently stable that they can be blended with acrylic monomer in useful proportions. However, in such situations, the presence of additional non-polymerizing reactants (e.g., the amine reactive compound) may result in other, undesirable affects.

For a two-part adhesive such as those of the invention to be most easily used in commercial and industrial environments, the ratio at which the two parts are combined should be a convenient whole number. This facilitates application of the adhesive with conventional, commercially available dispensers. Such dispensers are shown in U.S. Pat. Nos. 4,538,920 and 5,082,147 and are available from Conprotec, Inc. (Salem, N.H.) under the tradename "Mixpac". Typically, these dispensers use a pair of tubular receptacles arranged side-by-side with each tube being intended to receive one of the two parts of the adhesive. Two plungers, one for each tube, are simultaneously advanced (e.g., manually or by a hand-actuated ratcheting mechanism) to evacuate the contents of the tubes into a common, hollow, elongated mixing chamber that may also contain a static mixer to facilitate blending of the two parts. The blended adhesive is extruded from the mixing chamber onto a substrate. Once the tubes have been emptied, they can be replaced with fresh tubes and the application process continued.

The ratio at which the two parts of the adhesive are combined is controlled by the diameter of the tubes. (Each plunger is sized to be received within a tube of fixed diameter, and the plungers are advanced into the tubes at the same speed.) A single dispenser is often intended for use with a variety of different two-part adhesives and the plungers are sized to deliver the two parts of the adhesive at a convenient mix ratio. Some common mix ratios are 1:1, 2:1, 4:1 and 10:1.

If the two parts of the adhesive are combined in an odd mix ratio (e.g. 100:3.5), then the ultimate user would probably manually weigh the two parts of the adhesive. Thus, for best commercial and industrial utility and for ease of use with currently available dispensing equipment, the two parts of the adhesive should be capable of being combined in a common, whole number mix ratio such as 10:1 or less, more preferably 4:1, 3:1, 2:1 or 1:1.

Adhesive compositions of the invention are uniquely suited for use with conventional, commercially available dispensing equipment for two-part adhesives. The organoborane polyamine complexes of the invention have a relatively high molecular weight (as compared to other known organoborane amine complexes). Consequently, the complex can comprise essentially all of the second part of the adhesive while still providing an effective amount of organoborane in a useful whole number mix ratio of 10:1 or less.

Once the two parts have been combined, the composition should be used quickly, as the useful pot life may be short depending upon the acrylic monomer mix, the amount of complex, and the temperature at which the bonding is to be performed.

The polymerizable composition is applied to one or both substrates and then the substrates are joined together with pressure to force excess composition out of the bond line. This also has the advantage of displacing composition that has been exposed to air and that may have begun to oxidize.

In general, the bonds should be made shortly after the composition has been applied, preferably within about 10 minutes. The typical bond line thickness is about 0.1 to 0.3 mm. The bonding process can easily be carried out at room temperature and to improve the degree of polymerization it is desirable to keep the temperature below about 40° C., preferably below 30° C., and most preferably below about 25° C.

The bonds will cure to a reasonable green strength to permit handling of the bonded components within about 2 to 3 hours. Full strength will be reached in about 24 hours under ambient conditions; post-curing with heat (typically about 80° C.) may be used if desired.

When bonding fluoroplastics, it is advantageous to cool the first part of the two-part composition to about 0° to 5° C. before adding the organoborane polyamine complex. The bond should be made as soon after the composition has been applied as practical; performing the bonding operation at less than room temperature is also helpful.

The invention will be more fully appreciated with reference to the following nonlimiting examples in which (unless noted otherwise) all weights are given as weight percents (weight %), based on the total weight of the composition which is 100 weight %, and are reported to two significant digits following the decimal point.

Examples that were subsequently evaluated to measure the lap shear strength of the adhesive bonds were tested as described below.

Lap Shear Strength Test Method

The test specimens used were similar to that described in ASTM D-1002 except that the specimens were generated using finger panels of nominal dimensions 1 in.×4 in.×⅛ in. thick (2.5 cm×10.2 cm×0.3 cm thick). 0.5 in. (1.3 cm) wide red lithographers tape was applied to the end of one of the adherends in order to help fixture the bond and also to aid in making the lap region to be 0.5 in. (1.3 cm). Short pieces of 6 mil (0.15 mm) diameter piano wire were cut for use as spacers to control the thickness of the adhesive bondline.

The adhesive was prepared by weighing the monomer mixture into a vial that was capable of being sealed with a poly cap. Organoborane polyamine initiator complex was then added, blended with the monomer mixture using a wooden stick, and the vial was sealed with the poly cap. In general, the addition of organoborane polyamine amine initiator complex to the monomer mixture caused the mixture to slightly exotherm and, in some cases, turn yellow. A dab of the mixed adhesive was applied to each adherend and spread to make sure that a 1 in.×0.5 in. (2.5 cm×1.3 cm) area was covered at the end of each adherend. Two pieces of piano wire were placed into the adhesive on one adherend and the bond was closed and fixtured with the lithographers tape. The bond was further fixtured with two binder clips and allowed to cure at room temperature for 48 hours at which time the binder clips and tape were removed.

Lap shear testing was done with three types of adherends: mechanical grade TEFLON, high density polyethylene, and polypropylene, as available from Precision Punch and Plastic Co. (Minneapolis, Minn.). Three adhesive bonds were made with each adherend and each adhesive combination. For each adhesive, the TEFLON was bonded first, then the high density polyethylene, and then the polypropylene. After curing, the bonds were tested to failure using a Tensile Testing Machine. The crosshead speed was 0.1 in./minute (2.5 mm/min.) and the tests were carried out at room temperature. Bonds were visually inspected after being loaded to failure to determine the failure mode. Failure of the adherends is the most preferred although cohesive failure of the composition evidences a useful formulation.

Failure modes are reported in the examples based on a series of coded abbreviations which may be interpreted as follows:

| Abbreviation | Failure Mode |
|---|---|
| a | Good filet adhesion |
| b | One or more bonds stretched to yield of the adherend without failure |
| c | Mixed mode failure |
| d | Failure of the adherend |
| e | Cohesive failure within the adhesive |
| f | Adhesion failure of the adhesive |
| g | Incomplete wetting; puddling of the adhesive |

EXAMPLE 1

In example 1 organoborane polyamine complexes were synthesized. All glassware was washed and fired at 1000° F. (538° C.) or was fired by means of a Bunsen burner until the glassware glowed orange. A polyethylene glove bag was set up in the hood and was flushed with nitrogen. (In some cases, the synthesis was carried out in a glove box which had been inerted with nitrogen.) The glove bag or glove box contained a pressure equalizing dropping funnel, an electric balance, a flask with appropriate stoppers, and a stand.

The polyoxyalkylenepolyamine was degassed by freeze-thaw cycles under vacuum and was then weighed into the flask. The organoborane was weighed into the pressure equalizing dropping funnel and then added dropwise to the polyamine with stirring and cooling. A mild exotherm was observed and the reaction mixture was alternately clear and cloudy. The addition of the organoborane was moderated to control the exotherm. In some cases, fuming occurred and the addition of the borane was slowed until the fuming had subsided. Once all of the organoborane had been added, the flask was allowed to equilibrate to room temperature until either a liquid or a crystalline mass was obtained. If a crystalline mass was obtained, it was heated to 55° C. by means of an oil bath outside of the glove bag to liquify it so that it could be transferred. A hazy white liquid resulted which was poured into a vial previously flushed with nitrogen. After cooling, a white crystalline material was obtained. If the result was not a crystalline mass, then the liquid was poured from the flask into a bottle and sealed.

Complexes were made with the organoboranes and polyamines that are listed below in Table 1. For each complex the boron atom to nitrogen atom ratio was 1:1 (i.e., one mole of trialkyl borane for each equivalent of amine functionality.)

The complexes were examined for pyrophoricity. Drops of liquid samples were placed on paper towels which were then placed in a fume hood. The samples were observed for 24 hours. Any ignition is noted in Table 1. In one case, the catalyst did not ignite the paper towel until the paper was rubbed against a waxed floor. Most of the organoborane polyamine complexes of the invention are air stable and do not ignite combustible materials.

TABLE 1

| Complex Designation | Polyamine | Organo-borane | Calculated Molecular Weight of the Complex | Calculated % Boron in the Complex | Appearance of Complex | Comments |
|---|---|---|---|---|---|---|
| A | Diethylene glycol bis propyl amine (H221) | Tri-n-butyl borane | 584 | 3.73 | Clear yellowish liquid | No ignition |
| B | Diethylene glycol bis propyl amine (H221) | Tri-ethyl borane | 416 | 5.24 | Clear liquid which may solidify | No ignition |
| C | Polypropylene oxide diamine (Jeffamine D-230) | Tri-n-butyl borane | 594 | 3.67 | Clear liquid | Smoked when applied to paper |
| D | Polypropylene oxide diamine (Jeffamine D-230) | Tri-ethyl borane | 426 | 5.11 | Clear liquid | Ignited paper |
| E | Polypropylene oxide diamine (Jeffamine D-400) | Tri-n-butyl borane | 768 | 2.84 | Clear liquid | No ignition |
| F | Polypropylene oxide diamine (Jeffamine D-400) | Tri-ethyl borane | 600 | 3.63 | Clear yellowish liquid | Ignited if liquid was placed on paper and then rubbed against a waxed floor |
| G | Poly(ethylene oxide-co-propylene oxide) diamine (Jeffamine ED-600) | Tri-ethyl borane | 796 | 2.73 | Clear liquid | No ignition |
| H | Polypropylene oxide diamine (Jeffamine EDR-148) | Tri-n-butyl borane | 660 | 3.30 | Waxy crystalline solid | No ignition |
| I | Polypropylene oxide diamine (Jeffamine D-2000) | Tri-n-butyl borane | 2364 | 0.92 | Clear liquid | No ignition |
| J | Polypropylene oxide diamine (Jeffamine D-5000) | Tri-n-butyl borane | 5364 | 0.41 | Clear liquid | No ignition |
| K | Polypropylene oxide triamine (Jeffamine T-403) | Tri-ethyl borane | 636 | 3.42 | Clear, yellowish, viscous liquid | No ignition |

(H221 is commercially available from Union Carbide Company. The "Jeffamine" line of products is commercially available from Huntsman Chemical Company.)

EXAMPLE 2

A series of adhesive compositions was prepared using different complexes from Table 1 (each based on tri-n-butyl borane) and the following monomer mixture: 78 g of methyl methacrylate, 56 g of n-butyl acrylate, 60 g of medium molecular weight poly(methyl methacrylate)(101,000 molecular weight poly(methyl methacrylate-co-ethylacrylate) with less than 5% ethylacrylate from Aldrich Chemical Co.), and 6 g of methacrylic acid. The components of the monomer mixture were weighed into a 1 quart brown bottle that was then sealed and placed overnight in a Launder-o-meter that was set to 55° C. A light yellow to white, clear, moderately viscous solution resulted. This is referred to as Monomer Mixture A.

Using the techniques described above, 5 g of Monomer Mixture A were combined with various organoborane polyamine complexes to provide adhesive compositions that were tested for lap shear strength. In each case the complex provided about 0.2% by weight boron in the adhesive. The results are reported in Table 2 in pounds per square inch (psi).

TABLE 2

| Complex Designation | Complex Amount (g) | Weight % Boron in the Adhesive Composition | Lap Shear to TEFLON (psi) | Lap Shear to Polyethylene (psi) | Lap Shear to Polypropylene (psi) |
|---|---|---|---|---|---|
| C | 0.311 | 0.22 | 374 | 458 | 831 |
| A | 0.299 | 0.21 | 324 | 781 | 646 |
| H | 0.262 | 0.21 | 230 | 800 | 751 |

Example 2 shows that the organoborane polyamine complexes of the invention can be used to prepare acrylic adhesive compositions that provide high strength bonds to low surface energy plastic substrates. In some cases the lap shear strength exceeded the yield strength of the substrate.

EXAMPLE 3

Using the techniques described above, 5 g of Monomer Mixture A (see example 2) were combined with various organoborane polyamine complexes from Table 1 to provide adhesive compositions that were tested for lap shear strength. In each case the complex provided about 0.26% by weight boron in the adhesive and the complex was based on triethylborane rather than tri-n-butylborane as used in example 2. The results are reported below in Table 3.

The good adhesive performance evidenced by Table 4 was promoted by separately storing the monomers and the complex.

EXAMPLE 5

Using the methods described above, Monomer Mixture A (see example 2) was combined with various organoborane polyamine complexes from Table 1 to provide adhesive compositions that were tested for lap shear strength. In each case the complex and the monomer mix were blended at a weight ratio of 10:1 (i.e., 5 g Monomer Mixture A+0.5 g complex). The results are reported in Table 5.

TABLE 3

| Complex Designation | Complex Amount (g) | Lap Shear to TEFLON (psi) | Mode of Failure | Lap Shear to Polyethylene (psi) | Mode of Failure | Lap Shear to Polypropylene (psi) | Mode of Failure |
|---|---|---|---|---|---|---|---|
| B | 0.262 | 310 | a, c | 764 | e | 772 | d |
| D | 0.269 | 322 | a, c | 742 | e | 558 | e |
| F | 0.379 | 344 | b, a | 730 | e | 484 | e |

Table 3 indicates that useful adhesive compositions can also be made when the organoborane is triethylborane.

EXAMPLE 4

Organoborane polyamine complexes are prone to degradation during storage due to possible oxidation of the organoborane. However, as shown below, the complexes of the invention demonstrate excellent storage stability, even when kept under ambient, room temperature conditions for as long as six months.

More specifically, adhesive compositions similar to those in example 2 were prepared as described above except using organoborane polyamine complexes that had first been stored under ambient, room temperature conditions for about 6 months. Each example was based on 5 g of Monomer Mixture A and an amount of complex sufficient to provide about 0.21% by weight boron to the adhesive composition. The adhesive compositions were then prepared and tested as described in conjunction with example 2, with the results shown below in Table 4.

TABLE 4

| Complex Designation | Amount of Complex (g) | Lap Shear to TEFLON (psi) | Mode of Failure | Lap Shear to Polyethylene (psi) | Mode of Failure | Lap Shear to Polypropylene (psi) | Mode of Failure |
|---|---|---|---|---|---|---|---|
| A | 0.305 | 186 | a, f | 676 | e | 416 | a, c |
| H | 0.267 | 190 | a, f | 722 | e | 376 | a, c |
| C | 0.317 | 230 | a, f | 652 | e | 484 | e, d |

TABLE 5

| Complex Designation | Lap Shear to TEFLON (psi) | Wt. % Boron in Adhesive | Mode of Failure | Lap Shear to Polyethylene (psi) | Mode of Failure | Lap Shear to Polypropylene (psi) | Mode of Failure |
|---|---|---|---|---|---|---|---|
| A | 140 | 0.34 | a, f | 714 | e | 266 | a, f |
| E | 180 | 0.26 | a, c | 710 | e | 520 | d, a, c |
| C | 126 | 0.33 | c | 688 | e | 340 | a, c |
| B | 250 | 0.47 | a, c | 712 | e | 322 | c |
| F | 314 | 0.33 | a, e | 612 | e | 598 | a, e |
| D | 286 | 0.47 | a | 742 | e | 566 | e |

Table 5 shows that adhesive compositions according to the invention and which provide acceptable bond strengths and failure modes can be obtained when organoborane polyamine complexes are combined with acrylic monomers in an industrially useful 10:1 mix ratio.

EXAMPLE 6

In example 6, 5 g of Monomer Mix A were combined with different amounts of organoborane polyamine complexes B, F and K to vary the level of boron in the adhesive composition from 0.015% to 0.24%. The compositions were prepared and tested for lap shear strength using the techniques described above and with the results shown below in Table 6.

TABLE 6

| Complex Designation | Amount of Complex (g) | Weight % Boron in the Adhesive Composition | Lap Shear on TEFLON (psi) | Mode of Failure | Lap Shear on Polyethylene (psi) | Mode of Failure | Lap Shear on Polypropylene (psi) | Mode of Failure |
|---|---|---|---|---|---|---|---|---|
| B | 0.0144 | 0.015 | 1.3 | f,g | 2 | f,g | 6 | f,g |
| B | 0.0385 | 0.040 | 2.7 | c,g | 163 | c,e,g | 305 | c,e,g |
| B | 0.0974 | 0.10 | 348 | a,b,e | 576 | a,e | 586 | a,e |
| B | 0.236 | 0.24 | 342 | a,b,e | 642 | a,e | 516 | a,e |
| F | 0.0207 | 0.015 | 0 | f,g | 2.7 | f,g | 5.3 | f,g |
| F | 0.0557 | 0.040 | 200 | c,e | 352 | a,e | 380 | a,e |
| F | 0.141 | 0.10 | 342 | a,b,e | 468 | a,e | 464 | a,d,e |
| F | 0.347 | 0.24 | 290 | a,e | 550 | a,e | 474 | a,e |
| K | 0.0182 | 0.012 | 2 | f,g | 4 | f,g | 1.3 | f,g |
| K | 0.0489 | 0.033 | 197 | c,e,g | 152 | c,e,g | 74 | c,e,g |
| K | 0.124 | 0.83 | 355 | b | 324 | a,c,e | 505 | a,e |
| K | 0.292 | 0.19 | 347 | a,b,e | 204 | a,c,e | 477 | a,e |

Example 6 shows the effect on adhesion to low surface energy plastics when the level of boron in the adhesive composition is varied. Adhesive compositions according to the invention preferably include about 0.03 to 1.5 weight % boron based on the total weight of the adhesive composition, more preferably about 0.04 to 1.0 weight %, and most preferably about 0.1 to 0.3 weight,%. When the weight % boron is too low (i.e., less than 0.03 weight %), minimal adhesion is obtained to low surface energy plastics. At high levels of boron (e.g., higher than those used in example 6), adhesion is still good but the adhesive becomes increasingly porous due to the liberation of borane and, hence, are less desirable.

EXAMPLE 7

Example 7 describes the performance of a pair of known two-part acrylic adhesives, "DP-805" which is commercially available from the 3M Company (St. Paul, Minn.), and an adhesive that is intended to be based on U.S. Pat. No. 4,536,546, example 5 but using currently available materials (referred to herein as adhesive X). The formulation of adhesive X is as follows:

Part A:
35.5 parts HYPALON 30 (from E.I. duPont de Nemours)
53.2 parts methyl methacrylate
9.8 parts methacrylic acid
1 part cumene hydroperoxide
Part B:
25 parts BLENDEX B467 (acrylonitrile-butadiene-styrene terpolymer from General Electric Specialty Chemicals, Parkersburg, W. Va.)
75 parts methyl methacrylate
4.995 parts VANAX 808 (from Vanderbilt Chemical Co.)
0.005 part copper napthenate solution Part A was generated by mixing the components until a viscous solution resulted. Part B was generated by first mixing the graft co-polymer and the methyl methacrylate until a stable bluish dispersion resulted. The VANAX 808 and copper napthenate were then added. Adhesive bonds were made and tested for lap shear strength as described in conjunction with example 2 with the exception bonds were also made on 2024-T3 aluminum substrates according to the method described in ASTM D-1002. The results are shown below in Table 7.

TABLE 7

| | DP-805 | Adhesive X |
|---|---|---|
| Lap Shear on Aluminum (psi) | 3288 | 3688 |
| Lap Shear on TEFLON (psi) | 26 | 17 |
| Lap Shear on Polyethylene (psi) | 18 | 12 |
| Lap Shear on Polypropylene (psi) | 2.7 | 16 |

Table 7 shows that two-part acrylic adhesive compositions according to the invention which include an effective amount of boron (as provided by the organoborane polyamine complexes of the invention) have excellent adhesion to low surface energy plastics whereas other known two-part acrylic adhesives do not. However, the known adhesives do provide good adhesion to aluminum substrates. The known adhesives suffered cohesive failure with the aluminum substrates but failed adhesively with the polymeric substrates.

Various modifications and alterations of this invention will become apparent to those skilled in the art without departing from the scope and spirit of the invention. It should be understood that this invention is not limited to the illustrative embodiments set forth herein.

The embodiments for which an exclusive property or privilege is claimed are defined as follows:

1. A composite article comprising a first substrate, and a second substrate bonded to the first substrate by an acrylic adhesive, wherein the acrylic adhesive comprises the polymerization product of a polymerizable acrylic composition that comprised:
    a) at least one acrylic monomer;
    b) an effective amount of a complex comprising organoborane and polyoxyalkylenepolyamine; and
    c) an effective amount of a compound that was reactive with amine for liberating the organoborane to initiate polymerization of the at least one acrylic monomer.

2. A bonded composite according to claim 1 wherein the first substrate is a low surface energy polymer.

3. A bonded composite according to claim 2 wherein the first substrate is selected from the group consisting of polyethylene, polypropylene and polytetrafluoroethylene.

4. A bonded composite according to claim 3 wherein the second substrate is selected from the group consisting of polyethylene, polypropylene and polytetrafluoroethylene.

5. A bonded composite according to claim 2 wherein the second substrate is a low surface energy polymer.

6. A bonded composite according to claim 5 wherein the second substrate is selected from the group consisting of polyethylene, polypropylene and polytetrafluoroethylene.

7. A bonded composite according to claim 1 wherein the at least one acrylic monomer was selected from the group consisting of monofunctional acrylate ester, monofunctional methacrylate ester, substituted derivatives of the foregoing, and blends of the foregoing.

8. A bonded composite according to claim 7 wherein the monofunctional methacrylate ester was selected from the group consisting of methyl methacrylate, ethyl methacrylate, methoxy ethyl methacrylate, hydroxyethyl methacrylate, hydroxypropyl methacrylate, cyclohexyl methacrylate, tetrahydrofurfuryl methacrylate, and blends thereof.

9. A bonded composite according to claim 1 wherein the at least one acrylic monomer comprised a blend of alkyl methacrylate and alkyl acrylate.

10. A bonded composite according to claim 9 wherein the alkyl methacrylate was methyl methacrylate and the alkyl acrylate was butyl acrylate.

11. A bonded composite according to claim 1 wherein the acrylic adhesive further comprised an elastomeric modifier.

12. A bonded composite according to claim 1 wherein the acrylic adhesive composition comprised about 0.03 to 1.5 weight % boron.

13. A bonded composite according to claim 12 wherein the acrylic adhesive composition comprised about 0.1 to 0.3 weight % boron.

14. A bonded composite according to claim 1 wherein the compound that was reactive with amine was selected from the group consisting of acid, isocyanate, acid chloride, sulfonyl chloride, and aldehyde.

15. A bonded composite according to claim 1 wherein the complex had the structure

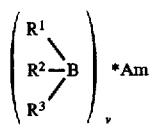

wherein:

$R^1$ was an alkyl group having 1 to 10 carbon atoms;

$R^2$ and $R^3$ were independently selected from alkyl groups having 1 to 10 carbon atoms and phenyl-containing groups;

Am was polyoxyalkylenepolyamine and had a structure selected from the group consisting of

and

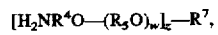

wherein:

$R^4$, $R^5$, and $R^6$ were alkylene groups having 1 to 10 carbon atoms and which were the same or which were different;

$R^7$ was the residue of a polyol;

w was $\geq 1$;

x was $\geq 0$;

y was $\geq 0$;

z was $> 2$; and the value of v was selected so as to provide an effective ratio of boron atoms to nitrogen atoms in the complex.

16. A bonded composite according to claim 15 wherein the compound that was reactive with amine was an acid.

17. A bonded composite according to claim 16 wherein the acid was a Lewis acid or a carboxylic acid.

18. A bonded composite according to claim 15 wherein the compound reactive with amine was acrylic acid or methacrylic acid.

19. A bonded composite according to claim 1 wherein:
    a) the at least one alkyl acrylate monomer was a blend of monomers comprising alkyl acrylate monomer and alkyl methacrylate monomer;
    b) the complex had the structure

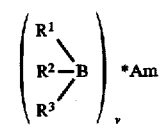

wherein:

$R^1$ was an alkyl group having 1 to 10 carbon atoms;

$R^2$ and $R^3$ were independently selected from alkyl groups having 1 to 10 carbon atoms and phenyl-containing groups;

Am was polyoxyalkylenepolyamine and had a structure selected from the group consisting of

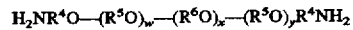

and

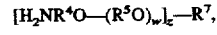

wherein:

$R^4$, $R^5$, and $R^6$ were alkylene groups having 1 to 10 carbon atoms and which were the same or which were different;

$R^7$ was the residue of a polyol;

the values of w, x, and y were selected such that the organoborane polyamine complex was a liquid at room temperature;

z was 3 or 4; and the value of v was selected such that the ratio of nitrogen atoms to boron atoms in the complex was about 1:1 to 2:1; and;

c) the compound that was reactive with amine was acrylic acid or methacrylic acid.

20. A bonded composite according to claim 19 wherein the first substrate is a low surface energy polymer.

21. A bonded composite according to claim 20 wherein the first substrate is selected from the group consisting of polyethylene, polypropylene and polytetrafluoroethylene.

22. A bonded composite according to claim 21 wherein the second substrate is selected from the group consisting of polyethylene, polypropylene and polytetrafluoroethylene.

23. A method of bonding a low surface energy polymer to a substrate, the method comprising the steps of:

a) providing a low surface energy polymer;

b) providing a substrate;

c) providing an adhesive composition comprising:
   i) at least one acrylic monomer;
   ii) an effective amount of a complex comprising organoborane and polyoxyalkylenepolyamine; and
   iii) an effective amount of a compound that is reactive with amine for liberating the organoborane to initiate polymerization of the at least one acrylic monomer;

d) applying the adhesive composition to either the low surface energy polymer or the substrate;

e) joining the low surface energy polymer and the substrate with the adhesive composition therebetween; and f) permitting the adhesive composition to cure to adhesively bond the low surface energy polymer and the substrate.

* * * * *

UNITED STATES PATENT AND TRADEMARK OFFICE
CERTIFICATE OF CORRECTION

PATENT NO.: 5,718,977

DATED: February 17, 1998

INVENTOR(S): Alphonsus V. Pocius

It is certified that error appears in the above-identified patent and that said Letters Patent is hereby corrected as shown below:

Column 24, line 16, "$H_2NR^4O\text{-}(R^5O)_w(R^6O)_x\text{-}(R^5O)_y\text{-}R^4NH_2$" should read
--$H_2NR^4O\text{-}(R^5O)_w\text{-}(R^6O)_x\text{-}(R^5O)_y\text{-}R^4NH_2$--.

Column 24, line 19, "$[H_2NR^4O\text{-}(R_5O)_w]_z\text{-}R7$" should read --$[H_2NR^4O\text{-}(R^5O)_w]_z\text{-}R7$--.

Column 24, line 60, "$H_2NR^4O\text{-}(R^5O)_w\text{-}(R^6O)_x\text{-}(R^5O)_yR^4NH_2$" should read
--$H_2NR^4O\text{-}(R^5O)_w\text{-}(R^6O)_x\text{-}(R^5O)_y\text{-}R^4NH_2$--.

Signed and Sealed this

Ninth Day of March, 1999

*Attest:*

Q. TODD DICKINSON

*Attesting Officer*   Acting Commissioner of Patents and Trademarks